Figure 4A:
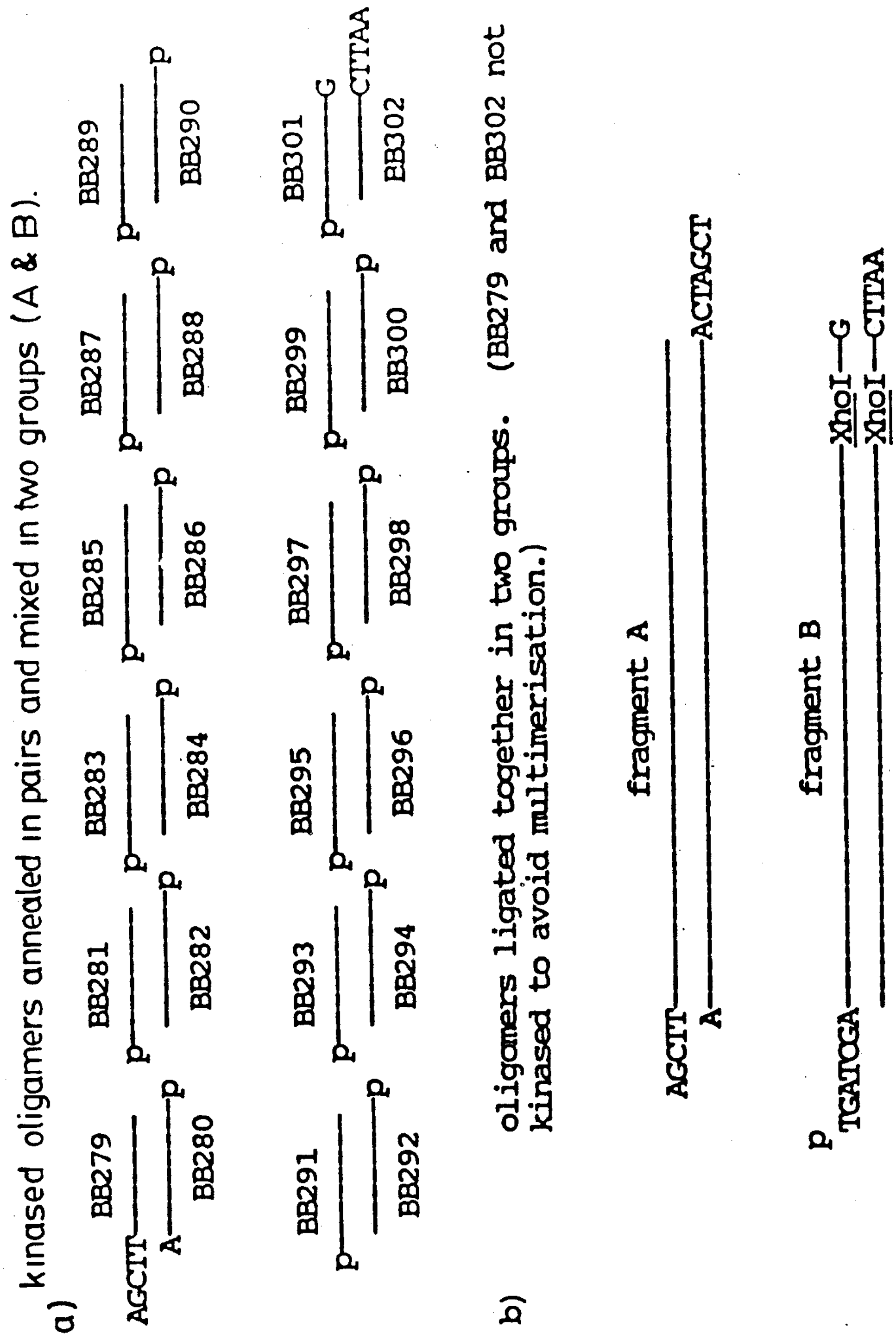

US005182376A

United States Patent [19]

[11] Patent Number: 5,182,376

Edwards et al.

[45] Date of Patent: Jan. 26, 1993

[54] DNA SEQUENCE FOR HORSERADISH PEROXIDASE C MODIFIED FOR EXPRESSION IN MAMMALIAN CELLS

[75] Inventors: Richard M. Edwards, Oxon; Julian F. Burke, East Sussex, both of England

[73] Assignee: British Bio-Technology Limited, England

[21] Appl. No.: 469,452

[22] PCT Filed: Oct. 7, 1988

[86] PCT No.: PCT/GB88/00833

§ 371 Date: Jun. 4, 1990

§ 102(e) Date: Jun. 4, 1990

[87] PCT Pub. No.: WO89/03424

PCT Pub. Date: Apr. 20, 1989

[30] Foreign Application Priority Data

Oct. 8, 1987 [GB] United Kingdom ................ 8723662

[51] Int. Cl.[5] ...................... C07H 15/12; C12P 21/06; C12N 9/08; C12N 15/00

[52] U.S. Cl. .................................. 536/23.2; 435/69.7; 435/192; 435/320.1; 935/10; 935/14; 935/34; 935/47

[58] Field of Search .................... 435/69.1, 252.3, 189, 435/192, 91; 536/27

[56] References Cited

PUBLICATIONS

Welinder (1976) Covalent Structure of the . . . Horseradish Peroxidase, FEBS Lett. 72, 19–23.

Suggs et al. (1981) Proced. Natl. Acd. Sci. 78, 6613–6617.

Maniatis (1983) Molecular Cloning, 412–413.

Kunkel (1985) Proced. Nat'l Acad. Sci. 82, 488.

*Primary Examiner*—Elizabeth C. Weimar
*Assistant Examiner*—Deborah Crouch

[57] ABSTRACT

Synthetic DNA coding for horseradish peroxidase includes the following sequence:

ATG CAG TTA ACC CCT ACA
TTC TAC GAC AAT AGC TGT
CCC AAC GTG TCC AAC ATC
GTT CGC GAC ACA ATC GTC
AAC GAG CTC AGA TCC GAT
CCC AGG ATC GCT GCT TCA
ATA TTA CGT CTG CAC TTC
CAT GAC TGC TTC GTG AAT
GGT TGC GAC GCT AGC ATA
TTA CTG GAC AAC ACC ACC
AGT TTC CGC ACT GAA AAG
GAT GCA TTC GGG AAC GCT
AAC AGC GCC AGG GGC TTT
CCA GTG ATC GAT CGC ATG
AAG GCT GCC GTT GAG TCA
GCA TGC CCA CGA ACA GTC
AGT TGT GCA GAC CTG CTG
ACT ATA GCT GCG CAA CAG
AGC GTG ACT CTT GCA GGC
GGA CCG TCC TGG AGA GTG
CCG CTC GGT CGA CGT GAC
TCC CTA CAG GCA TTC CTA
GAT CTG GCC AAC GCC AAC
TTG CCT GCT CCA TTC TTC
ACC CTG CCC CAG CTG AAG
GAT AGC TTT AGA AAC GTG
GGT CTG AAT CGC TCG AGT
GAC CTT GTG GCT CTG TCC (Abstract continued on next page.)

-continued

GGA GGA CAC ACA TTT GGA
AAG AAC CAG TGT AGG TTC
ATC ATG GAT AGG CTC TAC
AAT TTC AGC AAC ACT GGG
TTA CCT GAC CCC ACG CTG
AAC ACT ACG TAT CTC CAG
ACA CTG AGA GGC TTG TGC
CCA CTG AAT GGC AAC CTC
AGT GCA CTA GTG GAC TTT
GAT CTG CGG ACC CCA ACC
ATC TTC GAT AAC AAG TAC
TAT GTG AAT CTA GAG GAG
CAG AAA GGC CTG ATA CAG
AGT GAT CAA GAA CTG TTT

-continued

AGC AGT CCA AAC GCC ACT
GAC ACC ATC CCA CTG GTG
AGA AGT TTT GCT AAC TCT
ACT CAA ACC TTC TTT AAC
GCC TTC GTG GAA GCC ATG
GAC CGT ATG GGT AAC ATT
ACC CCT CTG ACG GGT ACC
CAA GGC CAG ATT CGT CTG
AAC TGC AGA GTG GTC AAC AGC AAC TCT TAA and incorporates useful restriction sites at frequent intervals to facilitate the cassette mutagenesis of selected regions. Also included are flanking restriction sites to simplify the incorporation of the gene into any desired expression system.

2 Claims, 25 Drawing Sheets

AAGCTTAACCATGCAGTTAACCCCTACATTCTACGACAATAGCTGTCCCAACGTGTCCAA

HindIII HpaI

TTCGAATTGGTACGTCAATTGGGGATGTAAGATGCTGTTATCGACAGGGTTGCACAGGTT 10 20 30 40 50 60

I V R D T I V N E L R S D P R I A A S I

CATCGTTCGCGACACAATCGTCAACGAGCTCAGATCCGATCCCAGGATCGCTGCTTCAAT

NruI SacI SspI

GTAGCAAGCGCTGTGTTAGCAGTTGCTCGAGTCTAGGCTAGGGTCCTAGCGACGAAGTTA 70 80 90 100 110 120

L R L H F H D C F V N G C D A S I L L D

ATTACGTCTGCACTTCCATGACTGCTTCGTGAATGGTTGCGACGCTAGCATATTACTGGA

NheI

TAATGCAGACGTGAAGGTACTGACGAAGCACTTACCAACGCTGCGATCGTATAATGACCT 130 140 150 160 170 180

N T T S F R T E K D A F G N A N S A R G

CAACACCACCAGTTTCCGCACTGAAAAGGATGCATTCGGGAACGCTAACAGCGCCAGGGG

NsiI

GTTGTGGTGGTCAAAGGCGTGACTTTTCCTACGTAAGCCCTTGCGATTGTCGCGGTCCCC 190 200 210 220 230 240

F P V I D R M K A A V E S A C P R T V S

CTTTCCAGTGATCGATCGCATGAAGGCTGCCGTTGAGTCAGCATGCCCACGAACAGTCAG

ClaI/PvuI SphI

GAAAGGTCACTAGCTAGCGTACTTCCGACGGCAACTCAGTCGTACGGGTGCTTGTCAGTC 250 260 270 280 290 300

C A D L L T I A A Q Q S V T L A G G P S

TTGTGCAGACCTGCTGACTATAGCTGCGCAACAGAGCGTGACTCTTGCAGGCGGACCGTC

BspMI FspI RsrII

AACACGTCTGGACGACTGATATCGACGCGTTGTCTCGCACTGAGAACGTCCGCCTGGCAG 310 320 330 340 350 360

W R V P L G R R D S L Q A F L D L A N A

CTGGAGAGTGCCGCTCGGTCGACGTGACTCCCTACAGGCATTCCTAGATCTGGCCAACGC

SalI BglII/BalI

GACCTCTCACGGCGAGCCAGCTGCACTGAGGGATGTCCGTAAGGATCTAGACCGGTTGCG 370 380 390 400 410 420

FIG. 2a-2

```
 N  L  P  A  P  F  F  T  L  P  Q  L  K  D  S  F  R  N  V  G
CAACTTGCCTGCTCCATTCTTCACCCTGCCCCAGCTGAAGGATAGCTTTAGAAACGTGGG
                                  PvuII
GTTGAACGGACGAGGTAAGAAGTGGGACGGGGTCGACTTCCTATCGAAATCTTTGCACCC
        430       440       450       460       470       480

 L  N  R  S  S  D  L  V  A  L  S  G  G  H  T  F  G  K  N  Q
TCTGAATCGCTCGAGTGACCTTGTGGCTCTGTCCGGAGGACACACATTTGGAAAGAACCA
        XhoI                      BspMII
AGACTTAGCGAGCTCACTGGAACACCGAGACAGGCCTCCTGTGTGTAAACCTTTCTTGGT
        490       500       510       520       530       540

 C  R  F  I  M  D  R  L  Y  N  F  S  N  T  G  L  P  D  P  T
GTGTAGGTTCATCATGGATAGGCTCTACAATTTCAGCAACACTGGGTTACCTGACCCCAC
                                              BstEII
CACATCCAAGTAGTACCTATCCGAGATGTTAAAGTCGTTGTGACCCAATGGACTGGGGTG
        550       560       570       580       590       600

 L  N  T  T  Y  L  Q  T  L  R  G  L  C  P  L  N  G  N  L  S
GCTGAACACTACGTATCTCCAGACACTGAGAGGCTTGTGCCCACTGAATGGCAACCTCAG
        SnaBI                             PflMI
CGACTTGTGATGCATAGAGGTCTGTGACTCTCCGAACACGGGTGACTTACCGTTGGAGTC
        610       620       630       640       650       660

 A  L  V  D  F  D  L  R  T  P  T  I  F  D  N  K  Y  Y  V  N
TGCACTAGTGGACTTTGATCTGCGGACCCCAACCATCTTCGATAACAAGTACTATGTGAA
ApaLI/SpeI                                        ScaI
ACGTGATCACCTGAAACTAGACGCCTGGGGTTGGTAGAAGCTATTGTTCATGATACACTT
        670       680       690       700       710       720

 L  E  E  Q  K  G  L  I  Q  S  D  Q  E  L  F  S  S  P  N  A
TCTAGAGGAGCAGAAAGGCCTGATACAGAGTGATCAAGAACTGTTTAGCAGTCCAAACGC
XbaI            StuI            BclI
AGATCTCCTCGTCTTTCCGGACTATGTCTCACTAGTTCTTGACAAATCGTCAGGTTTGCG
        730       740       750       760       770       780

 T  D  T  I  P  L  V  R  S  F  A  N  S  T  Q  T  F  F  N  A
CACTGACACCATCCCACTGGTGAGAAGTTTTGCTAACTCTACTCAAACCTTCTTTAACGC
        BstXI
GTGACTGTGGTAGGGTGACCACTCTTCAAAACGATTGAGATGAGTTTGGAAGAAATTGCG
        790       800       810       820       830       840
```

FIG. 2a-3

```
  F  V  E  A  M  D  R  M  G  N  I  T  P  L  T  G  T  Q  G  Q
CTTCGTGGAAGCCATGGACCGTATGGGTAACATTACCCCTCTGACGGGTACCCAAGGCCA
          NcoI                                  KpnI
GAAGCACCTTCGGTACCTGGCATACCCATTGTAATGGGGAGACTGCCCATGGGTTCCGGT
       850       860       870       880       890       900

  I  R  L  N  C  R  V  V  N  S  N  S  *  *
GATTCGTCTGAACTGCAGAGTGGTCAACAGCAACTCTTAATAAGGATCCGAATTC
           PstI                              BamHI EcoRI
CTAAGCAGACTTGACGTCTCACCAGTTGTCGTTGAGAATTATTCCTAGGCTTAAG
       910       920       930       940       950
```

FIG. 2b

| ENZYME | SEQUENCE | POSITION |
|---|---|---|
| HindIII | AAGCTT | 1 |
| HpaI | GTTAAC | 16 |
| SacI | GAGCTC | 86 |
| SspI | AATATT | 118 |
| NheI | GCTAGC | 164 |
| NsiI | ATGCAT | 210 |
| ClaI | ATCGAT | 251 |
| PvuI | CGATCG | 253 |
| SphI | GCATGC | 281 |
| BspMI | ACCTGC | 309 |
| FspI | TGCGCA | 325 |
| RsrII | CGGACCG | 352 |
| SalI | GTCGAC | 378 |
| BglII | AGATCT | 406 |
| BalI | TGGCCA | 411 |
| PvuII | CAGCTG | 452 |
| XhoI | CTCGAG | 490 |
| BspMII | TCCGGA | 512 |
| BstEII | GGTTACC | 585 |
| SnaBI | TACGTA | 610 |
| PflMI | CCACTGAATGG | 641 |
| ApaLI | GTGCAC | 660 |
| SpeI | ACTAGT | 664 |
| ScaI | AGTACT | 708 |
| XbaI | TCTAGA | 721 |
| StuI | AGGCCT | 736 |
| BclI | TGATCA | 751 |
| BstXI | CCATCCCACTGG | 789 |
| NcoI | CCATGG | 852 |
| KpnI | GGTACC | 887 |
| PstI | CTGCAG | 913 |
| BamHI | GGATCC | 944 |
| EcoRI | GAATTC | 950 |

FIG. 2c

```
            M  Q  L  T  P  T  F  Y  D  N  S  C  P  N  V  S  N
AAGCTTAACCATGCAGTTAACCCCTACATTCTACGACAATAGCTGTCCCAACGTGTCCAA
HindIII      HpaI
TTCGAATTGGTACGTCAATTGGGGATGTAAGATGCTGTTATCGACAGGGTTGCACAGGTT
        10        20        30        40        50        60

 I  V  R  D  T  I  V  N  E  L  R  S  D  P  R  I  A  A  S  I
CATCGTTCGCGACACAATCGTCAACGAGCTCAGATCCGATCCCAGGATCGCTGCTTCAAT
     NruI              SacI                                SspI
GTAGCAAGCGCTGTGTTAGCAGTTGCTCGAGTCTAGGCTAGGGTCCTAGCGACGAAGTTA
        70        80        90       100       110       120

 L  R  L  H  F  H  D  C  F  V  N  G  C  D  A  S  I  L  L  D
ATTACGTCTGCACTTCCATGACTGCTTCGTGAATGGTTGCGACGCTAGCATATTACTGGA
                                                NheI
TAATGCAGACGTGAAGGTACTGACGAAGCACTTACCAACGCTGCGATCGTATAATGACCT
       130       140       150       160       170       180

 N  T  T  S  F  R  T  E  K  D  A  F  G  N  A  N  S  A  R  G
CAACACCACCAGTTTCCGCACTGAAAAGGATGCATTCGGGAACGCTAACAGCGCCAGGGG
                              NsiI
GTTGTGGTGGTCAAAGGCGTGACTTTTCCTACGTAAGCCCTTGCGATTGTCGCGGTCCCC
       190       200       210       220       230       240

 F  P  V  I  D  R  M  K  A  A  V  E  S  A  C  P  R  T  V  S
CTTTCCAGTGATCGATCGCATGAAGGCTGCCGTTGAGTCAGCATGCCCACGAACAGTCAG
         ClaI/PvuI                        SphI
GAAAGGTCACTAGCTAGCGTACTTCCGACGGCAACTCAGTCGTACGGGTGCTTGTCAGTC
       250       260       270       280       290       300

 C  A  D  L  L  T  I  A  A  Q  Q  S  V  T  L  A  G  G  P  S
TTGTGCAGACCTGCTGACTATAGCTGCGCAACAGAGCGTGACTCTTGCAGGCGGACCGTC
        BspMI        FspI                              RsrII
AACACGTCTGGACGACTGATATCGACGCGTTGTCTCGCACTGAGAACGTCCGCCTGGCAG
       310       320       330       340       350       360
```

FIG. 2c cont'd

```
 W  R  V  P  L  G  R  R  D  S  L  Q  A  F  L  D  L  A  N  A
CTGGAGAGTGCCGCTCGGTCGACGTGACTCCCTACAGGCATTCCTAGATCTGGCCAACGC
                  SalI                          BglII/BalI
GACCTCTCACGGCGAGCCAGCTGCACTGAGGGATGTCCGTAAGGATCTAGACCGGTTGCG
        370       380       390       400       410       420

 N  L  P  A  P  F  F  T  L  P  Q  L  K  D  S  F  R  N  V  G
CAACTTGCCTGCTCCATTCTTCACCCTGCCCCAGCTGAAGGATAGCTTTAGAAACGTGGG
                                     PvuII
GTTGAACGGACGAGGTAAGAAGTGGGACGGGGTCGACTTCCTATCGAAATCTTTGCACCC
        430       440       450       460       470       480

 L  N  R  S
TCTGAATCGCTCGAGGAATTC
         XhoI  EcoRI
AGACTTAGCGAGCTCCTTAAG
        490
```

FIG. 2d

```
                S   S   D   L   V   A   L   S   G   G   H   T   F   G   K   N   Q
 AAGCTTAACTCGAGTGACCTTGTGGCTCTGTCCGGAGGACACACATTTGGAAAGAACCA
HindIII  XhoI                 BspMII
 TTCGAATTGAGCTCACTGGAACACCGAGACAGGCCTCCTGTGTGTAAACCTTTCTTGGT
        490       500       510       520       530       540

 C   R   F   I   M   D   R   L   Y   N   F   S   N   T   G   L   P   D   P   T
GTGTAGGTTCATCATGGATAGGCTCTACAATTTCAGCAACACTGGGTTACCTGACCCCAC
                                                 BstEII
CACATCCAAGTAGTACCTATCCGAGATGTTAAAGTCGTTGTGACCCAATGGACTGGGGTG
        550       560       570       580       590       600

 L   N   T   T   Y   L   Q   T   L   R   G   L   C   P   L   N   G   N   L   S
GCTGAACACTACGTATCTCCAGACACTGAGAGGCTTGTGCCCACTGAATGGCAACCTCAG
        SnaBI                              PflMI
CGACTTGTGATGCATAGAGGTCTGTGACTCTCCGAACACGGGTGACTTACCGTTGGAGTC
        610       620       630       640       650       660

 A   L   V   D   F   D   L   R   T   P   T   I   F   D   N   K   Y   Y   V   N
TGCACTAGTGGACTTTGATCTGCGGACCCCAACCATCTTCGATAACAAGTACTATGTGAA
ApaLI/SpeI                                           ScaI
ACGTGATCACCTGAAACTAGACGCCTGGGGTTGGTAGAAGCTATTGTTCATGATACACTT
        670       680       690       700       710       720

 L   E   E   Q   K   G   L   I   Q   S   D   Q   E   L   F   S   S   P   N   A
TCTAGAGGAGCAGAAAGGCCTGATACAGAGTGATCAAGAACTGTTTAGCAGTCCAAACGC
XbaI           StuI           BclI
AGATCTCCTCGTCTTTCCGGACTATGTCTCACTAGTTCTTGACAAATCGTCAGGTTTGCG
        730       740       750       760       770       780
```

FIG. 2d cont'd

T D T I P L V R S F A N S T Q T F F N A

CACTGACACCATCCCACTGGTGAGAAGTTTTGCTAACTCTACTCAAACCTTCTTTAACGC

BstXI

GTGACTGTGGTAGGGTGACCACTCTTCAAAACGATTGAGATGAGTTTGGAAGAAATTGCG 790 800 810 820 830 840

F V E A M D R M G N I T P L T G T Q G Q

CTTCGTGGAAGCCATGGACCGTATGGGTAACATTACCCCTCTGACGGGTACCCAAGGCCA

NcoI KpnI

GAAGCACCTTCGGTACCTGGCATACCCATTGTAATGGGGAGACTGCCCATGGGTTCCGGT 850 860 870 880 890 900

I R L N C R V V N S N S * *

GATTCGTCTGAACTGCAGAGTGGTCAACAGCAACTCTTAATAAGGATCCGAATTC

PstI BamHI EcoRI

CTAAGCAGACTTGACGTCTCACCAGTTGTCGTTGAGAATTATTCCTAGGCTTAAG 910 920 930 940 950

```
                         BB279
5' AGCTTAACCATGCAGTTAACCCCTACATTCTACGACAATAGCTG    TCCCAACGTGTCCAA
       |||||||||||||||||||||||||||||||||||||||        ||||||||
3'     ATTGGTACGTCAATTGGGGATGTAAGATGCTGTTATCGACAGGGTTG  CACAGGTT
        10        20        30        40        50        60
                         BB280

      BB281                                   BB283
CATCGTTCGCGACACAATCGTCAACG   AGCTCAGATCCGATCCCAGGATCGCTGCTTCAAT
||||||||||||||||||||||||||               ||||||||||||||||||||||||||
GTAGCAAGCGCTGTGTTAGCAGTTGCTCGAGTC   TAGGCTAGGGTCCTAGCGACGAAGTTA
     70        80        90        100       110       120
      BB282                                   BB284

                          BB285
ATTACGTC   TGCACTTCCATGACTGCTTCGTGAATGGTTGCGACGCTAG   CATATTACTGGA
||||||||        ||||||||||||||||||||||||||||||||||         |||||
TAATGCAGACGTGAA   GGTACTGACGAAGCACTTACCAACGCTGCGATCGTATAAT   GACCT
     130       140       150       160       170       180
                          BB286

        BB287                                  BB289
CAACACCACCAGTTTCCGCACTGAAAAGG   ATGCATTCGGGAACGCTAACAGCGCCAGGGG
|||||||||||||||||||||||||||||             ||||||||||||||||||||||
GTTGTGGTGGTCAAAGGCGTGACTTTTCCTACGTAA   GCCCTTGCGATTGTCGCGGTCCCC
     190       200       210       220       230       240
        BB288                                  BB290

                          BB291
CTTTCCAG   TGATCGATCGCATGAAGGCTGCCGTTGAGTCAGCATGCCCAC   GAACAGTCAG
||||||||        ||||||||||||||||||||||||||||||||||||         |||
GAAAGGTCACTAGCT   AGCGTACTTCCGACGGCAACTCAGTCGTACGGGTGCTTGTCA   GTC
     250       260       270       280       290       300
                          BB292
```

FIG. 3a

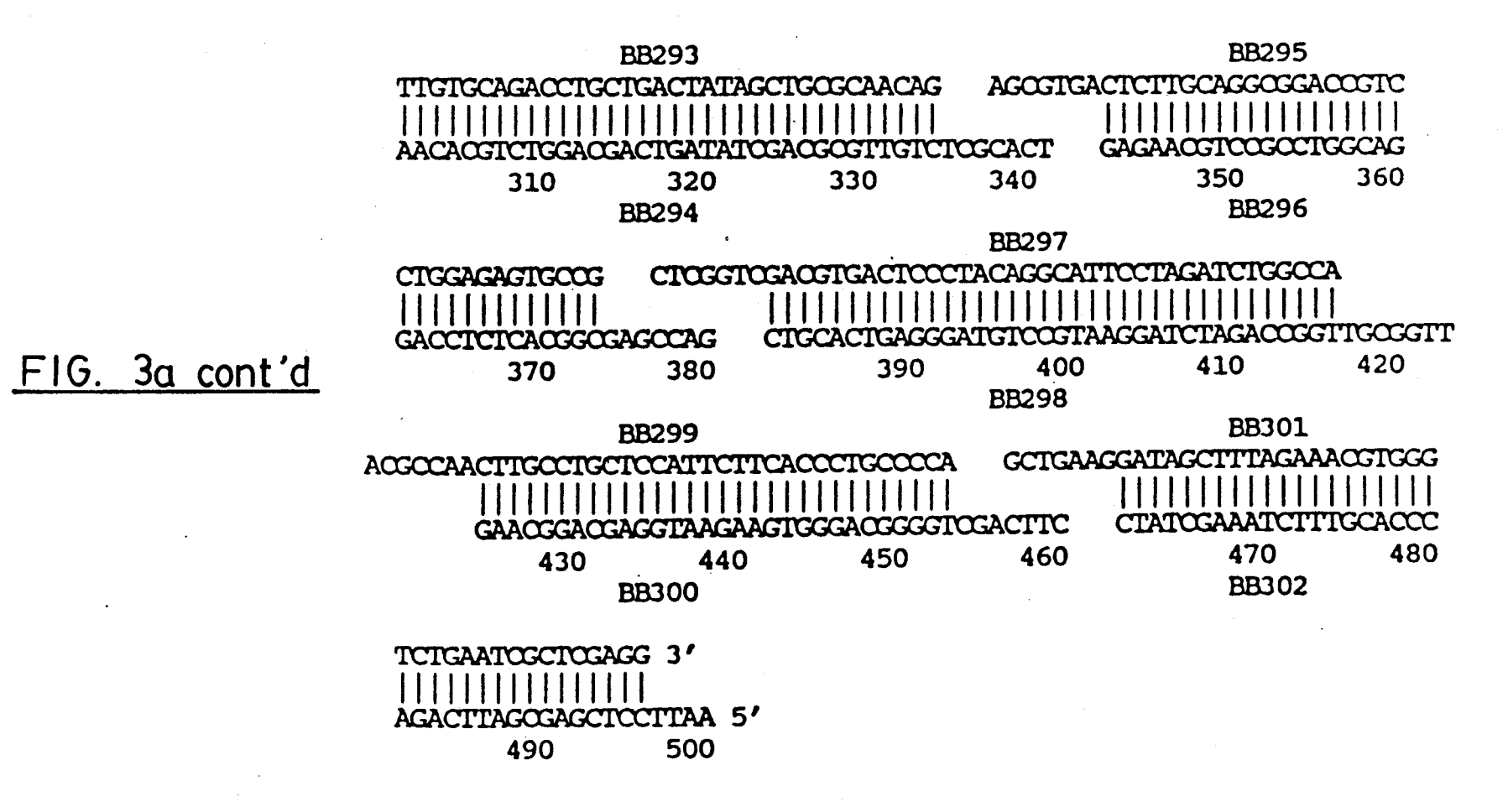

BB293 BB295

TTGTGCAGACCTGCTGACTATAGCTGCGCAACAG AGCGTGACTCTTGCAGGCGGACCGTC

AACACGTCTGGACGACTGATATCGACGCGTTGTCTCGCACT GAGAACGTCCGCCTGGCAG 310 320 330 340 350 360

BB294 BB296

BB297

CTGGAGAGTGCCG CTCGGTCGACGTGACTCCCTACAGGCATTCCTAGATCTGGCCA

GACCTCTCACGGCGAGCCAG CTGCACTGAGGGATGTCCGTAAGGATCTAGACCGGTTGCGGTT 370 380 390 400 410 420

BB298

BB299 BB301

ACGCCAACTTGCCTGCTCCATTCTTCACCCTGCCCCA GCTGAAGGATAGCTTTAGAAACGTGGG

GAACGGACGAGGTAAGAAGTGGGACGGGGTCGACTTC CTATCGAAATCTTTGCACCC 430 440 450 460 470 480

BB300 BB302

TCTGAATCGCTCGAGG 3'

AGACTTAGCGAGCTCCTTAA 5'

490 500

FIG. 3a cont'd

```
                             BB303
5'  AGCTTAACTCGAGTGACCTTGTGGCTCTGTCCGGAGGACACACATTT   GGAAAGAACCA
        ||||||||||||||||||||||||||||||||||||||||||           ||||
 3'     ATTGAGCTCACTGGAACACCGAGACAGGCCTCCTGTGTGTAAACCTTTCT   TGGT
        490       500       510       520       530          540
                             BB304

          BB305                                        BB307
GTGTAGGTTCATCATGGATAGGCTCTACAA    TTTCAGCAACACTGGGTTACCTGACCCCAC
||||||||||||||||||||||||||||||           |||||||||||||||||||||||
CACATCCAAGTAGTACCTATCCGAGATGTTAAAGTCG    TTGTGACCCAATGGACTGGGGTG
        550       560       570          580       590       600
          BB306                                        BB308

                                         BB309
GCTGAACACTACGTA    TCTCCAGACACTGAGAGGCTTGTGCCCACTGAATGGCAACCTC
|||||||||||||||              ||||||||||||||||||||||||||||||||||
CGACTTGTGATGCATAGAGGTC       TGTGACTCTCCGAACACGGGTGACTTACCGTTGGAGTCACGTG
        610       620          630       640       650       660
                                         BB310

                     BB311
AGTGCACTAGTGGACTTTGATCTGCGGACCCCAACCATCTTCG   ATAACAAGTACTATGTGAA
      |||||||||||||||||||||||||||||||||||||            ||||||||||||
      ATCACCTGAAACTAGACGCCTGGGGTTGGTAGAAGCTATTGTT      CATGATACACTT
        670       680       690       700          710       720
                     BB312

          BB313                                        BB315
TCTAGAGGAGCAGAAAGGCCTGA    TACAGAGTGATCAAGAACTGTTTAGCAGTCCAAACGC
|||||||||||||||||||||||               ||||||||||||||||||||||||||||||
AGATCTCCTCGTCTTTCCGGACTATGTCTC        ACTAGTTCTTGACAAATCGTCAGGTTTGCG
        730       740       750          760       770       780
          BB314                                        BB316
```

FIG. 3b

```
                                  BB317
CACTGA    CACCATCCCACTGGTGAGAAGTTTTGCTAACTCTACTCAAA    CCTTCTTTAACGC
||||||          |||||||||||||||||||||||||||||||||||           ||||||
GTGACTGTGGTAG   GGTGACCACTCTTCAAAACGATTGAGATGAGTTTGGAAGAA    ATTGCG
     790        800       810       820       830       840
                          BB318

          BB319                                        BB321
CTTCGTGGAAGCCATGGACCGTATGGGTAACAT   TACCCCTCTGACGGGTACCCAAGGCCA
|||||||||||||||||||||||||||||||||           ||||||||||||||||||||
GAAGCACCTTCGGTACCTGGCATACCCATTGTAATGGGGA   GACTGCCCATGGGTTCCGGT
     850       860       870       880       890       900
          BB320                                        BB322

                                  BB323
GATTCGTCTGAACTGC   AGAGTGGTCAACAGCAACTCTTAATAAGGATCCG 3'
||||||||||||||||          ||||||||||||||||||||||||||
CTAAGCAGACTTGACGTCTCACC   AGTTGTCGTTGAGAATTATTCCTAGGCTTAA 5'
     910       920       930       940       950
                          BB324
```

FIG. 3b cont'd c) The ligations were checked for the presence of fragment A & B on 2% agarose gels then the ligation reactions were mixed and the reaction allowed to continue to give the final product.

```
AGCTT—————————————TGATCGA——————————XhoI—G
    A—————————————ACTAGCT——————————XhoI—CTTAA
```

d) The HRP gene fragment was isolated on a 2% LGT agarose gel and cloned into EcoRI/HindIII cut pUC18.

FIG. 4a cont'd

```
                        HRP 5' half                 p
vvvva     AGCTT———————————————————————————XhoI—G     aattcvvvvv
vvvvttcga     A———————————————————————————XhoI—CTTAA      gvvvvv
          p

     HindIII            HRP 5' half              EcoRI
  vvvvaAGCTT——————————————————————————————XhoI—Gaattcvvvvv
  vvvvttcgaA——————————————————————————————XhoI—CTTAAgvvvvv
```

v = vector sequence
p = 5' phosphates

FIG. 4b
a) kinased oligomers annealed in pairs and mixed in two groups (A & B).
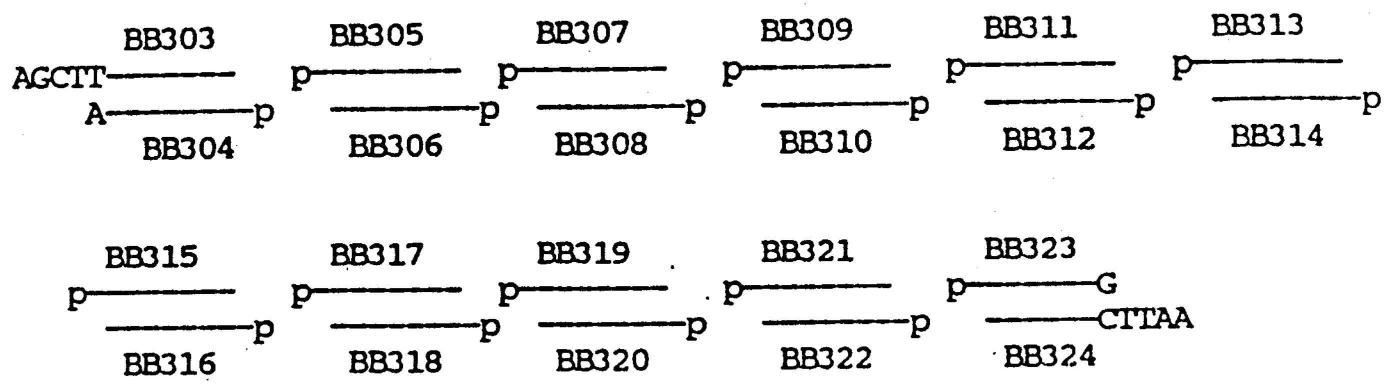
b) oligomers ligated together in two groups. (BB303 and BB324 not kinased to avoid multimerisation.
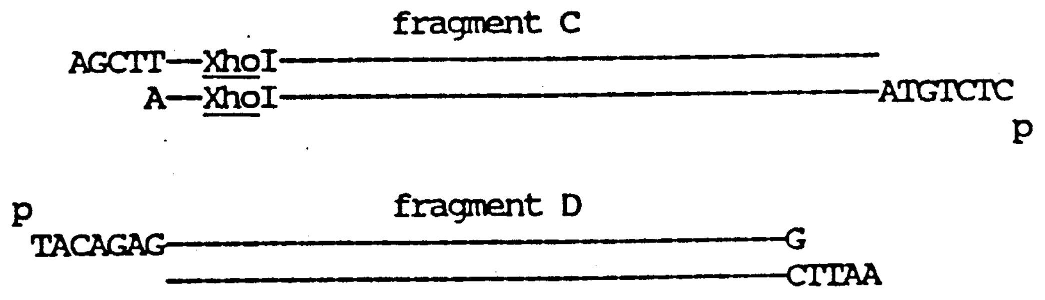

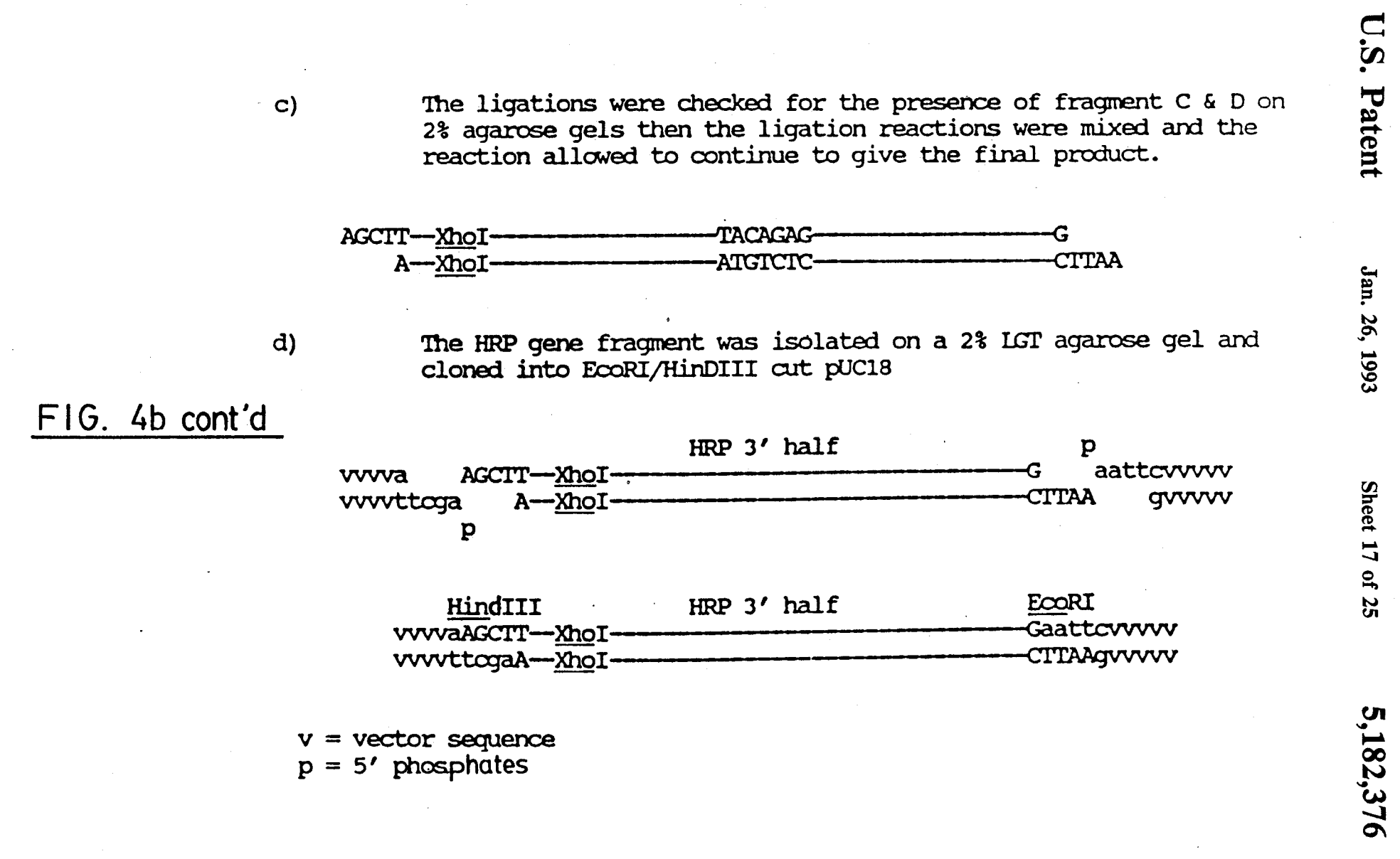

c) The ligations were checked for the presence of fragment C & D on 2% agarose gels then the ligation reactions were mixed and the reaction allowed to continue to give the final product.

```
AGCTT—XhoI———————————TACAGAG———————————G
    A—XhoI———————————ATGTCTC———————————CTTAA
```

d) The HRP gene fragment was isolated on a 2% LGT agarose gel and cloned into EcoRI/HinDIII cut pUC18

FIG. 4b cont'd

```
                      HRP 3' half              p
vvvva     AGCTT—XhoI————————————————————G    aattcvvvvv
vvvvttcga     A—XhoI————————————————————CTTAA    gvvvvv
          p

      HindIII         HRP 3' half          EcoRI
      vvvvaAGCTT—XhoI——————————————————————Gaattcvvvvv
      vvvvttcgaA—XhoI——————————————————————CTTAAgvvvvv
```

v = vector sequence
p = 5' phosphates

Figure 4C:
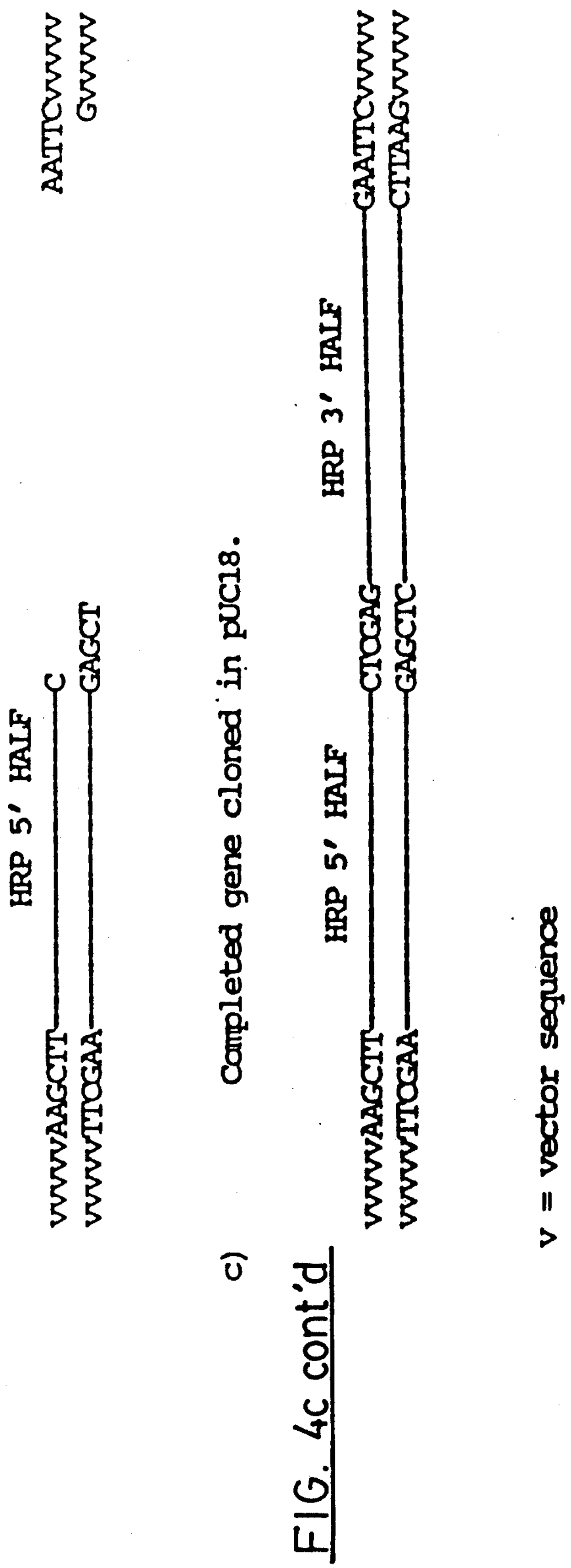

FIG. 4c
a) 5′ and 3′ clones of HRP cloned in pUC18 were digested with XhoI and EcoRI. Relevant fragments from each digest were isolated from a 0.8% LGT agarose gel.
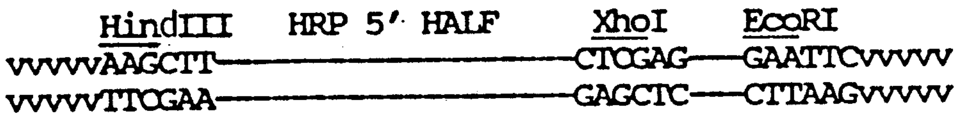
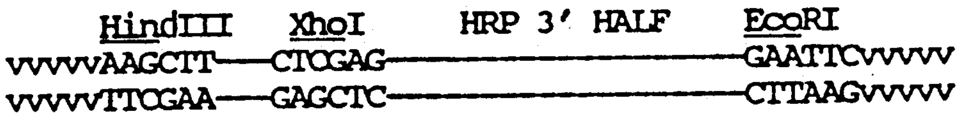
b) XhoI/EcoRI fragment carrying 3′ half of HRP ligated into XhoI/EcoRI cut HRP 5′ half clone.
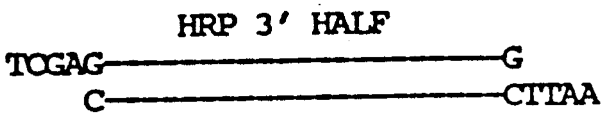

```
            M   k   c   s   w   v   i   f   f   l   m   a   v   v   t   g   v
AAGCTTCCACCATGAAGTGCTCCTGGGTGATCTTCTTCCTGATGGCCGTGGTGACCGGCG
         10        20        30        40        50        60

  n   s<>Q   L   T   P   T   F   Y   D   N   S   C   P   N   V   S   N   I   V
TGAACTCCCAGTTAACCCCTACATTCTACGACAATAGCTGTCCCAACGTGTCCAACATCG
         70HpaI    80        90       100       110       120

  R   D   T   I   V   N   E   L   R   S   D   P   R   I   A   A   S   I   L   R
TTCGCGACACAATCGTCAACGAGCTCAGATCCGATCCCAGGATCGCTGCTTCAATATTAC
        130       140       150       160       170       180

  L   H   F   H   D   C   F   V   N   G   C   D   A   S   I   L   L   D   N   T
GTCTGCACTTCCATGACTGCTTCGTGAATGGTTGCGACGCTAGCATATTACTGGACAACA
        190       200       210       220       230       240

  T   S   F   R   T   E   K   D   A   F   G   N   A   N   S   A   R   G   F   P
CCACCAGTTTCCGCACTGAAAAGGATGCATTCGGGAACGCTAACAGCGCCAGGGGCTTTC
        250       260       270       280       290       300

  V   I   D   R   M   K   A   A   V   E   S   A   C   P   R   T   V   S   C   A
CAGTGATCGATCGCATGAAGGCTGCCGTTGAGTCAGCATGCCCACGAACAGTCAGTTGTG
        310       320       330       340       350       360
```

FIG. 6

```
            M  k  c  s  w  v  l  f  f  l  m  a  v  v  t  g  v
AAGCTTCCACCATGAAGTGCTCCTGGGTGATCTTCTTCCTGATGGCCGTGGTGACCGGCG
        10        20        30        40        50        60

 n  s<>Q  L  T  P  T  F  Y  D  N  S  C  P  N  V  S  N  I  V
TGAACTCCCAGTTAACCCCTACATTCTACGACAATAGCTGTCCCAACGTGTCCAACATCG
        70HpaI    80        90       100       110       120

 R  D  T  I  V  N  E  L  R  S  D  P  R  I  A  A  S  I  L  R
TTCGCGACACAATCGTCAACGAGCTCAGATCCGATCCCAGGATCGCTGCTTCAATATTAC
       130       140       150       160       170       180

 L  H  F  H  D  C  F  V  N  G  C  D  A  S  I  L  L  D  N  T
GTCTGCACTTCCATGACTGCTTCGTGAATGGTTGCGACGCTAGCATATTACTGGACAACA
       190       200       210       220       230       240

 T  S  F  R  T  E  K  D  A  F  G  N  A  N  S  A  R  G  F  P
CCACCAGTTTCCGCACTGAAAAGGATGCATTCGGGAACGCTAACAGCGCCAGGGGCTTTC
       250       260       270       280       290       300

 V  I  D  R  M  K  A  A  V  E  S  A  C  P  R  T  V  S  C  A
CAGTGATCGATCGCATGAAGGCTGCCGTTGAGTCAGCATGCCCACGAACAGTCAGTTGTG
       310       320       330       340       350       360
```

FIG. 6a

```
  D  L  L  T  I  A  A  Q  Q  S  V  T  L  A  G  G  P  S  W  R
CAGACCTGCTGACTATAGCTGCGCAACAGAGCGTGACTCTTGCAGGCGGACCGTCCTGGA
        370       380       390       400       410       420

  V  P  L  G  R  R  D  S  L  Q  A  F  L  D  L  A  N  A  N  L
GAGTGCCGCTCGGTCGACGTGACTCCCTACAGGCATTCCTAGATCTGGCCAACGCCAACT
        430       440       450       460       470       480

  P  A  P  F  F  T  L  P  Q  L  K  D  S  F  R  N  V  G  L  N
TGCCTGCTCCATTCTTCACCCTGCCCCAGCTGAAGGATAGCTTTAGAAACGTGGGTCTGA
        490       500       510       520       530       540

  R  S  S  D  L  V  A  L  S  G  G  H  T  F  G  K  N  Q  C  R
ATCGCTCGAGTGACCTTGTGGCTCTGTCCGGAGGACACACATTTGGAAAGAACCAGTGTA
        550       560       570       580       590       600

  F  I  M  D  R  L  Y  N  F  S  N  T  G  L  P  D  P  T  L  N
GGTTCATCATGGATAGGCTCTACAATTTCAGCAACACTGGGTTACCTGACCCCACGCTGA
        610       620       630       640       650       660

  T  T  Y  L  Q  T  L  R  G  L  C  P  L  N  G  N  L  S  A  L
ACACTACGTATCTCCAGACACTGAGAGGCTTGTGCCCACTGAATGGCAACCTCAGTGCAC
        670       680       690       700       710       720
```

FIG. 6b

FIG. 6c

```
 V  D  F  D  L  R  T  P  T  I  F  D  N  K  Y  Y  V  N  L  E
TAGTGGACTTTGATCTGCGGACCCCAACCATCTTCGATAACAAGTACTATGTGAATCTAG
      730       740       750       760       770       780

 E  Q  K  G  L  I  Q  S  D  Q  E  L  F  S  S  P  N  A  T  D
AGGAGCAGAAAGGCCTGATACAGAGTGATCAAGAACTGTTTAGCAGTCCAAACGCCACTG
      790       800       810       820       830       840

 T  I  P  L  V  R  S  F  A  N  S  T  Q  T  F  F  N  A  F  V
ACACCATCCCACTGGTGAGAAGTTTTGCTAACTCTACTCAAACCTTCTTTAACGCCTTCG
      850       860       870       880       890       900

 E  A  M  D  R  M  G  N  I  T  P  L  T  G  T  Q  G  Q  I  R
TGGAAGCCATGGACCGTATGGGTAACATTACCCCTCTGACGGGTACCCAAGGCCAGATTC
      910       920       930       940       950       960

 L  N  C  R  V  V  N  S  N  S  l  l  h  d  m  v  e  v  v  d
GTCTGAACTGCAGAGTGGTCAACAGCAACTCTCTACTCCATGATATGGTGGAGGTCGTTG
      PstI      980       990      1000      1010      1020

 f  v  s  s  m  *  *
ACTTTGTTAGCTCTATGTAATAAGGATCCGAATTC
     1030      1040        EcoRI
```

KEY

Underlined sequences indicate linkers used to adapt synthetic gene.

Lower case residues indicate N and C terminal pre & pro sequences.

DNA SEQUENCE FOR HORSERADISH PEROXIDASE C MODIFIED FOR EXPRESSION IN MAMMALIAN CELLS

This invention relates to synthetic genes coding for horseradish peroxidase.

Horseradish peroxidase C (E.C.1.11.1.7) (HRP) is the major peroxidase isozyme isolated from the horseradish (*Armoracia rusticana*). It is a monomeric glycoprotein of 308 amino acids the polypeptide chain having a MW of 33,980 D. There are three neutral carbohydrate side chains and 4 disulphide bridges. The amino acid sequence of the mature protein has been determined. The presence of a pyrrolidonecarboxylyl amino terminus indicates that the protein is probably produced as a precursor form that is processed on secretion. The active form of the enzyme contains a hemin prosthetic group.

The enzyme is particularly stable and is amenable to crosslinking and derivitisation without excessive loss of activity. This together with its wide range of chromogenic substrates, some of which give rise to insoluble, chemiluminescent or flourescent products, and the low background activities observed in most applications, have made horseradish peroxidase an invaluable tool for diagnostic and research applications in the fields of immunology, histochemistry, cytology and molecular biology. A further advantage it presents over other enzymatic markers is that some some substrates for the enzyme give rise to electron dense products that allow correlation of peroxidase location with cellular ultrastructure using electron microscopy. In addition, horseradish peroxidase is electron dense itself by virtue of the Fe it contains and as a result can act as an E.M. marker in its own right. Particular applications have been found in immunochemistry, where peroxidase cross linked to immunoglobulin is widely used in both ELISA based assay systems and immunocytochemistry. Methods have been described that use either direct crosslinking of peroxidase to the immunoglobulin or indirect crosslinking of biotin labelled immunoglobulin to a streptavidin/horseradish peroxidase complex. Such streptavidin complexes have also found widespread application in nucleic acid hybridisation methods where biotinylated probe sequences can be localised by sequential incubation with the streptavidin/peroxidase complex and a suitable chromogenic peroxidase substrate.

The amino acid sequence of horseradish peroxidase is taught by Welinder, K. G. (*Eur. J. Biochem.* 96, 483–502 (1979)). The cloning of the cDNA or natural gene for horseradish peroxidase has not been described.

In order to facilitate the dissection of the structure/function relationships of HRP, its incorporation into expression vectors and the production of novel chimeric proteins containing HRP functionality an improved novel synthetic gene for the peroxidase C produced by *Armoracia rusticana* is sought.

It is by no means easy to predict the design of an improved HRP gene, since the factors that determine the expressibility of a given DNA sequence are still poorly understood. Furthermore, the utility of the gene in various applications will be influenced by such considerations as codon usage and restriction sites. The present invention relates to a synthetic HRP gene which has advantages in the ease with which it can be modified due to the presence of useful restriction sites.

When synthesising and assembling genes, problems have been encountered when there are inverted or direct repeats greater than eight bases long in the genetic sequence. In addition, areas of unbalanced base composition such as G/C or A/T rich regions or polypurine/polypyrimidine tracts have been found to lead to inefficient expression. :The present invention seeks to overcome or at least alleviate these difficulties.

According to a first aspect of the invention, there is provided DNA coding for HRP and having restriction sites for the following enzymes:

HpaI, SacI, SspI, NheI, NsiI, ClaI, PvuI, SphI,

BspMI, FspI, RsrII, SalI, BglII, BalI, PvuII,

XhoI, BspMII, BstEII, SnaBI, PflMI, ApaLI, SpeI,

ScaI, XbaI, StuI, BclI, BstXI, NcoI, KpnI, and

PstI.

The DNA may also contain a 5′ HindIII site and/or a 5′ NdeI site and/or a 3′ BamHI site and/or a 3′ EcoRI site.

According to a second aspect of the invention, there is provided DNA including the following sequence:

CAG TTA ACC CCT ACA TTC TAC GAC AAT AGC TGT CCC
AAC GTG TCC AAC ATC GTT CGC GAC ACA ATC GTC AAC
GAG CTC AGA TCC GAT CCC AGG ATC GCT GCT TCA ATA
TTA CGT CTG CAC TTC CAT GAC TGC TTC GTG AAT GGT
TGC GAC GCT AGC ATA TTA CTG GAC AAC ACC ACC AGT
TTC CGC ACT GAA AAG GAT GCA TTC GGG AAC GCT AAC
AGC GCC AGG GGC TTT CCA GTG ATC GAT CGC ATG AAG
GCT GCC GTT GAG TCA GCA TGC CCA CGA ACA GTC AGT
TGT GCA GAC CTG CTG ACT ATA GCT GCG CAA CAG AGC
GTG ACT CTT GCA GGC GGA CCG TCC TGG AGA GTG CCG
CTC GGT CGA CGT GAC TCC CTA CAG GCA TTC CTA GAT
CTG GCC AAC GCC AAC TTG CCT GCT CCA TTC TTC ACC
CTG CCC CAG CTG AAG GAT AGC TTT AGA AAC GTG GGT

-continued

CTG AAT CGC TCG AGT GAC CTT GTG GCT CTG TCC GGA
GGA CAC ACA TTT GGA AAG AAC CAG TGT AGG TTC ATC
ATG GAT AGG CTC TAC AAT TTC AGC AAC ACT GGG TTA
CCT GAC CCC ACG CTG AAC ACT ACG TAT CTC CAG ACA
CTG AGA GGC TTG TGC CCA CTG AAT GGC AAC CTC AGT
GCA CTA GTG GAC TTT GAT CTG CGG ACC CCA ACC ATC
TTC GAT AAC AAG TAC TAT GTG AAT CTA GAG GAG CAG
AAA GGC CTG ATA CAG AGT GAT CAA GAA CTG TTT AGC
AGT CCA AAC GCC ACT GAC ACC ATC CCA CTG GTG AGA
AGT TTT GCT AAC TCT ACT CAA ACC TTC TTT AAC GCC
TTC GTG GAA GCC ATG GAC CGT ATG GGT AAC ATT ACC
CCT CTG ACG GGT ACC CAA GGC CAG ATT CGT CTG AAC
TGC AGA GTG GTC AAC AGC AAC TCT

The above sequence may be immediately preceeded by an initiation codon (ATG) and immediately followed by a termination codon (TAA), but this will not necessarily be the case if the DNA incorporates linker(s) and/or extension(s), such as a sequence coding for a signal peptide, for example for efficient expression in eukaryotic cells such as mammalian cells. One extension which gives good expression in mammalian cells is a 5' -extension coding for the amino acids KCSWVIFFLMAVVTGVNS, which may be provided between an initiation codon and the codon coding for the first Q residue. A preferred such extension is shown in FIG. 6. A sequence coding for a 3'-signal sequence may code for LLHDMVEVVDFVSSM; a preferred DNA sequence coding for this series of amino acid residues is also shown in FIG. 6.

A synthetic HRP gene as described above incorporates useful restriction sites at frequent intervals to facilitate the cassette mutagenesis of selected regions. Also included in preferred embodiments are flanking restriction sites to simplify the incorporation of the gene into any desired expression system.

Codons are those that are favoured by *E. coli* but it is expected that the DNA would be suitable for expression in other organisms including yeast and mammalian cells.

According to a third aspect of the invention, there is provided a genetic construct comprising DNA according to the first or second aspect or a fragment thereof. The fragment may comprise at least 10, 20, 30, 40 or 50 nucleotides. A genetic construct in accordance with the third aspect may be a vector, such as a plasmid, cosmid or phage.

According to a fourth aspect of the invention, there is provided a process for the preparation of DNA in accordance with the first or second aspect or a genetic construct in accordance with the third aspect, the process comprising coupling successive nucleotides and/or ligating appropriate oligomers.

The invention also relates to other nucleic acid (including RNA) either corresponding to or complementary to DNA in accordance with the first or second aspects.

The invention encompasses a process for the production of monodisperse horseradish peroxidase C comprising the expression of at least part of a genetic construct as described above.

Further, the invention extends to constructs as described above comprising all or a fragment of a sequence in accordance with the first or second aspect fused to any other sequence of DNA so as to result in a sequence capable of encoding a hybrid protein possessing peroxidase activity. An example of such a construct is a genetic fusion between a gene encoding horseradish peroxidase and a gene encoding streptavidin or avidin such that the encoded fusion protein possesses both biotin binding and peroxidase activity. Another example is a genetic fusion between a gene encoding horseradish peroxidase and a gene encoding an immunoglobulin-derived antigen binding function such that the fusion protein possesses both antigen binding and horseradish peroxidase activity. The antigen binding function may be an immunoglobulin heavy chain or light chain or fragments thereof or an engineered monomeric antigenic recognition site.

Particular constructs of interest include: vectors comprising the gene for horseradish peroxidase C that enable the production of fusions between horseradish peroxidase and any other protein of interest; and expression vectors that provide for the co-expression of the gene for horseradish peroxidase and another gene of interest either as a single fusion product, as a single polycistronic message or as two separate but linked transcriptional units.

According to a further aspect of the invention, there is provided a gene for horseradish peroxidase containing a mutation (either missense, nonsense, deletion, insertion, duplication or other rearrangement) that destroys or impairs the activity of the encoded horseradish peroxidase protein. The invention extends to genetic constructs including all or a fragment of such a mutant horseradish peroxidase gene.

Defective or non-defective horseradish peroxidase genetic constructas can be employed (for example as markers) in mammalian cells and/or in transgenic animals.

Specific applications of synthetic genes for horseradish peroxidase, which themselves form further aspects of the invention, are disclosed in greater detail below:

1) The gene can be incorporated into a suitable expression vector to allow for the efficient production of the enzyme in a compatible organism. This will have the advantage of being a ready source of a monodisperse enzyme preparation free of the contaminating isozymes present in the material isolated from horseradish root. Varying the organism or cell type chosen for production will also allow for the production of HRP with different patterns of glycosylation, including no glycosylation. Such material will have better defined properties that will make it more suitable for more demanding histochemical applications and sensitive enzyme assays, especially immunoassays.

2) The gene can be incorporated into an HRP-streptavidin or HRP-avidin gene fusion. This will allow for the production of streptavidin-HRP or avidin-HRP complexes without the need for cross-linking. Again this will allow for a better defined, more stable product and will probably result in less loss of both biotin binding and peroxidase activity.

3) Similarly, fusions between immunoglobulins and HRP or protein A and HRP can be produced that would be valuable histochemical reagents. Again the need for the usual cross-linking procedures would be avoided.

4) The HRP gene would have valuable applications in the construction of vectors designed to allow the production of fusions between HRP and any other protein for which a gene or cDNA had been cloned or for which the amino acid sequence is known. This would be useful both for monitoring the expression of a gene the product of which is difficult to assay and to tag the protein of interest to allow its metabolism and pharmodynamics to be followed in vivo by the use of the appropriate histochemical techniques or enzyme assays. Additionally, HRP fusions will allow for a simple immunopurification of the fusion product through the use of an appropriate anti-HRP antibody.

5) The expression of HRP will be a useful marker in expression systems, e.g. mammalian cell expression systems. The HRP gene could be expressed either as a fusion or on a polycistronic message with the gene of interest, or as a separate but closely linked transcriptional unit. The production of the easily assayed HRP could be readily screened for and used as an indication as to which clones of cells were likely to be expressing large quantities of the desired product. The use of fluorescent or chemiluminescent HRP chromogenic substrates would allow for the possibility of directly selecting high producing eukaryotic cells by fluorescence activated cell-sorting (FACS).

6) HRP genes carrying mutations (missense, nonsense, deletion, insertion, duplication or other rearrangement) that destroy or impair the enzymatic activity of the resultant product would allow the construction of vectors that could be used to follow the frequency of reversion or suppression of the particular mutation introduced into the gene.

The introduction of such defective HRP genes into the germ line of the organism of interest would also enable a researcher to fate-map particular cell-types by histologically examining the pattern of HRP activity in the tissue of interest. Care would have to be excercised in constructing a mutant HRP gene with the correct in vivo reversion rate so that areas of HRP activity and hence the presence of reverted HRP gene could be taken as evidence for the clonal origin of the HRP+ cells. The intact synthetic non-mutant gene could also be used for such fate-mapping experiments by infection of an organism with the HRP gene in a siutable vector such as a retroviral vector or transposon.

7) The advantage of a synthetic gene for HRP allows for the production of HRP genes modified to encode a protein carrying small additional sequences, such as N- or C- terminal extensions. These will be of great application in simplifying the purification of the HRP and/or increasing the ease and enhancing the specificity with which it can be cross-linked to other proteins of interest or otherwise derivatised. For example, a C-terminal extension of six to eight Arg residues could be used to simplify purification by analogy with the technique of Sassenfeld et al. *Bio/technology* 2 76 (1984). Alternatively, a tail of Lys residues would provide an accessible and sensitive site for reaction with bifunctional cross-linking reagents such as glutaraldehyde.

Figure 5:
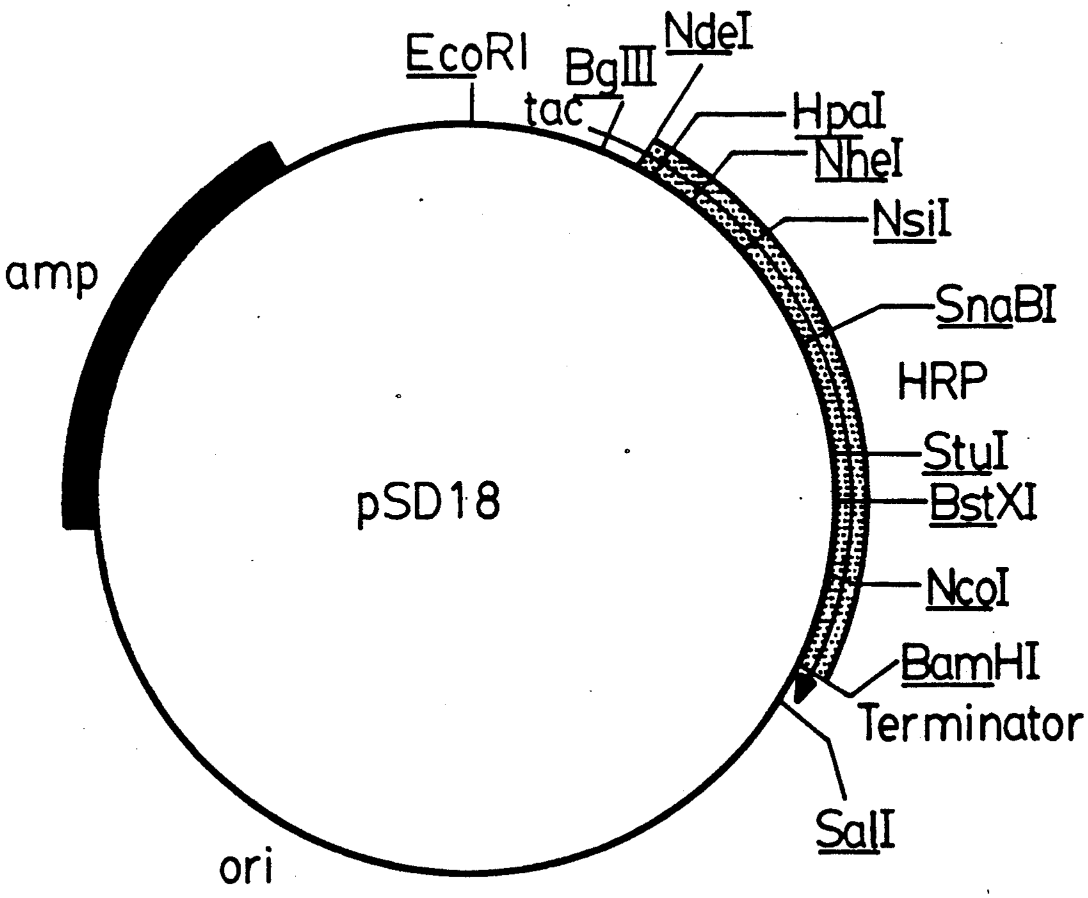
Figure 7:
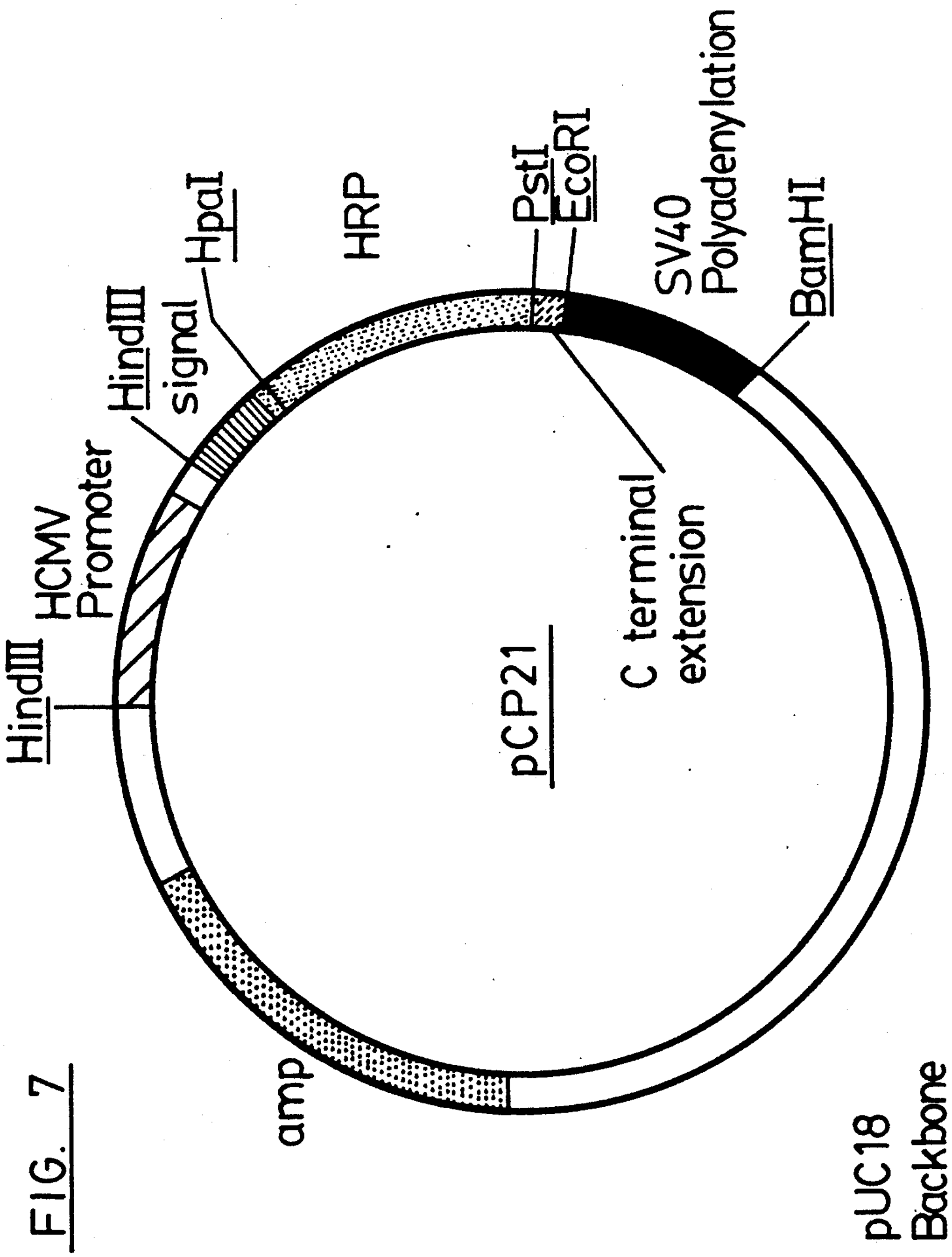

Preferred embodiments and examples of the invention will now be described. In the following description, reference is made to a number of drawings, in which:

Figure 1:
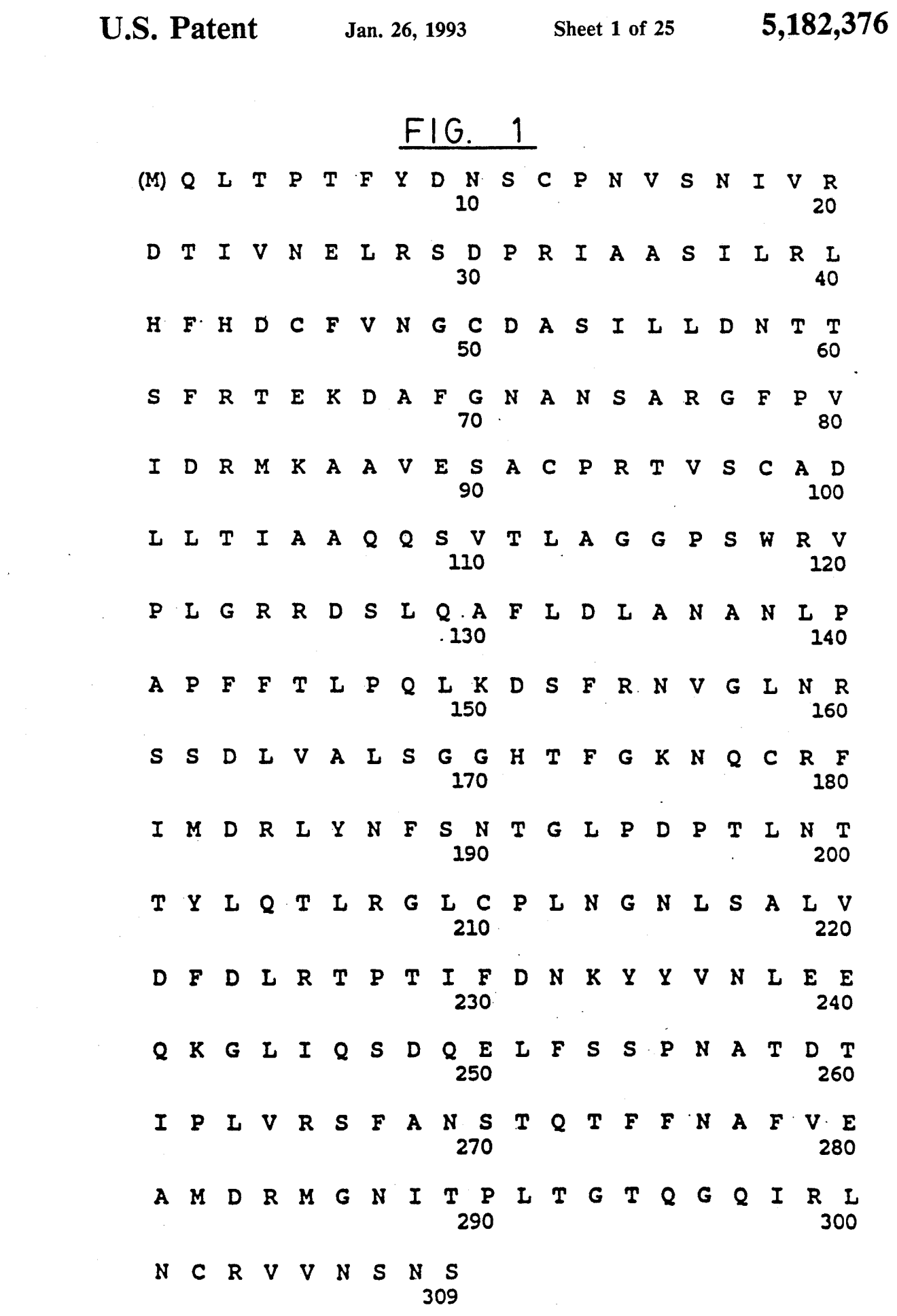

FIG. 1, shows the amino acid sequence of horseradish peroxidase C;

FIGS. 2*a–d* shows the sequence of the horseradish peroxidase synthetic gene; a summary of useful restriction sites; and a sequence of front and back halves of the gene that were initially cloned;

FIGS. 3*a–b* shows a sequence of synthetic horseradish peroxidase gene divided into oligonucleotides;

FIGS. 4*a–c* shows a summary of assembly procedure used;

FIG. 5 shows the structure of the HRP *E. coli* expression plasmid pSD18;

FIGS. 6*a–c* shows a synthetic HRP gene modified for efficient expression in mammalian cells; and FIG. 7 shows the structure of the HRP mammalian expression plasmid pCP21.

EXAMPLE 1

The gene was designed to be synthesised and cloned, in this example, in two halves with a final sub-cloning step to yield the full length gene. The sequence of the two halves of the gene together with that of the final product are depicted in FIG. 2. The final synthetic gene encodes the entire mature horseradish peroxidase protein together with the required initiator methionine residue but lacks the leader sequence that is assumed to be present in the natural gene. It is envisaged that the leader sequence appropriate to the expression system of choice would be added to the synthetic gene as required or ommitted to allow for intracellular expression of the gene.

The desired gene sequence was divided into a front half and a back half of 501 and 474 bp respectively. Both halves were designed with a common XhoI site to allow for the complete gene to be assembled with a simple cloning step. The front and back halves of the gene were divided into 24 and 22 oligodeoxyribonucleotides (oligomers) respectively as depicted in FIG. 3. The division was such as to provide 7 base cohesive ends after annealing complementary pairs of oligomers. The end points of the oligomers were chosen to minimise the potential for inappropriate ligation of oligomers at the assembly stage.

The oligomers were synthesised by automated solid phase phosphoramidite chemistry. Following de-blocking and removal from the controlled pore glass support the oligomers were purified on denaturing polyacrylamide gels, further purified by ethanol precipitation and finally dissolved in water prior to estimation of their concentration.

All the oligomers with the exception of the 5' terminal oligomers BB279 and BB302 for the front half and BB303 and BB324 for the back half were then kinased to provide them with a 5' phosphate as required for the ligation step. Complementary oligomers were then annealed and the oligomers ligated together by T4 DNA ligase as depicted in FIG. 4. The ligation products were separated on a 2% low gelling temperature (LGT) gel and the bands corresponding to the front and back halves of the horseradish peroxidase gene were cut out and extracted from the gel. The purified fragments were then ligated separately to EcoRI/HindIII cut DNA of the plasmid vector pUC18. The ligated products were transformed into HW87 and plated on L-agar plates containing 100 mcg $ml^{-1}$ ampicillin. Colonies containing potential clones were then grown up in L-broth containing ampicillin at 100 mcg $ml^{-1}$ and plasmid DNA isolated. Positive clones were identified by direct dideoxy sequence analysis of the plasmid DNA using the 17 base universal primer, a reverse sequencing primer complementary to the opposite strand on the other side of the polylinker and some of the oligomers employed in the assembly of the gene that served as internal primers. One front half and one back half clone were subsequently re-sequenced on both strands to confirm that no mutations were present. The complete gene was then assembled by isolating the 466 bp XhoI-EcoRI fragment from the back half calone that contained the 3' end of the gene and ligating it to a front half clone that had also been digested with EcoRI and XhoI. The identity of the final construct was confirmed by restriction analysis and subsequent complete resequencing.

All the techniques of genetic manipulation used in the manufacture of this gene are well known to those skilled in the art of genetic engineering. A description of most of the techniques can be found in one of the following laboratory manuals: *Molecular Cloning* by T. Maniatis, E. F. Fritsch and J. Sambrook published by Cold Spring Harbor Laboratory, Box 100, New York, USA, or *Basic Methods in Molecular Biology* by L. G. Davis, M. D. Dibner and J. F. Battey published by Elsevier Science publishing Co. Inc. New York, USA.

Additional and modified methodologies are detailed below.

1) Oligonucleotide Synthesis

The oligonuoleotides were synthesised by automated phosphoramidite chemistry using cyanoethyl phosphoramidtes. The methodology is now widely used and has been described (Beaucage, S. L. and Caruthers, M. H. *Tetrahedron Letters.* 24, 245 (1981)).

2) Purification of Oligonucleotides

The oligonucleotides were de-protected and removed from the CPG support by incubation in concentrated NH3. Typically, 50 mg of CPG carrying 1 micromole of oligonucleotide was de-protected by incubation for 5 hr at 70° in 600 mcl of concentrated $NH_3$. The supernatant was transferred to a fresh tube and the oligomer precipitated with 3 volumes of ethanol. Following oentrifugation the pellet was dried and resuspended in 1 ml of water. The concentration of crude oligomer was then determined by measuring the absorbance at 260 nm.

For gel purification 10 absorbance units of the crude oligonucleotide were dried down and resuspended in 15 mcl of marker dye (90% de-ionised formamide, 10 mM tris, 10 mM borate, 1 mM EDTA, 0.1% bromophenol blue). The samples were heated at 90° for 1 minute and then loaded onto a 1.2 mm thick denaturing polyacrylamide gel with 1.6 mm wide slots. The gel was prepared from a stock of 15% acrylamide, 0.6% bisacrylamide and 7M urea in 1 X TBE and was polymerised with 0.1% ammonium persulphate and 0.025% TEMED. The gel was pre-run for 1 hr. The samples were run at 1500 V for 4–5 hr. The bands were visualised by UV shadowing and those corresponding to the full length product cut out and transferred to micro-testubes. The oligomers were eluted from the gel slice by soaking in AGEB (0.5M ammonium acetate, 0.01M magnesium acetate and 0.1% SDS) overnight. The AGEB buffer was then transferred to fresh tubes and the oligomer precipitated with three volumes of ethanol at −70° for 15 min. The precipitate was collected by centrifugation in an Eppendorf microfuge for 10 min, the pellet washed in 80% ethanol, the purified oligomer dried, redissolved in 1 ml of water and finally filtered through a 0.45 micron micro-filter. The concentration of purified product was measured by determining its absorbance at 260 nm.

3) Kinasing of Oligomers 250 pmole of oligomer was dried down and resuspended in 20 mcl kinase buffer (70 mM Tris pH 7.6, 10 mM MgCl2, 1 mM ATP, 0.2 mM spermidine, 0.5 mM dithiothreitol). 10 u of T4 polynucleotide kinase was added and the mixture incubated at 37° for 30 min. The kinase was then inactivated by heating at 85° for 15 min.

4) Annealing 8 mcl of each oligomer was mixed, heated to 90° and then slow cooled to room temperature over a period of an hour.

5) Ligation 5 mcl of each annealed pair of oligomers were mixed and 10 X ligase buffer added to give a final ligase reaction mixture (50 mM Tris pH 7.5, 10 mM $MgCl_2$, 20 mM dithiothreitol, 1 mM ATP. T4 DNA ligase was added at a rate of 100 u per 50 mcl reaction and ligation carried out at 15° for 4 hr.

6) Agarose Gel Electrophoresis

Ligation products were separated using 2% low gelling temperature agarose gels in 1 X TBE buffer (0.094M Tris pH8.3, 0.089M boric acid, 0.25 mM EDTA) containing 0.5 mcg $ml^{-1}$ ethidium bromide.

7) Isolation of Ligation Products

The band corresponding to the expected horseradish peroxidase gene or gene fragment ligation product was identified by reference to size markers under long wave UV illumination. The band was cut out of the gel and the DNA extracted as follows.

The volume of the gel slice was estimated from its weight and then melted by incubation at 65° for 10 min. The volume of the slice was then made up to 400 mcl with TE (10 mM Tris pH 8.0, 1 mM EDTA) and Na acetate added to a final concentration of 0.3M. 10 mcg of yeast tRNA was also added as a carrier. The DNA was then subjected to three rounds of extraction with equal volumes of TE equilibrated phenol followed by three extractions with ether that had been saturated with water. The DNA was precipitated with 2 volumes of ethanol, centrifuged for 10 min in a microfuge, the pellet washed in 70% ethanol and finally dried down. The DNA was taken up in 20 mcl of TE and 2 mcl run on a 2% agarose gel to estimate the recovery of DNA.

8) Cloning of Fragments

For the initial cloning of the two halves of horseradish peroxidase 0.5 mcg of pUC18 DNA was prepared by cleavage with HindIII and EcoRI as advised by the suppliers. The digested DNA was run on an 0.8% LGT gel and the vector band purified as described above. For the final assembly step the clone carrying the front half of the horseradish peroxidase gene was treated similarly using the enzymes XhoI and EcoRI.

20 ng of cut vector DNA was then ligated to various peroxidase gene DNA ranging from 2 to 20 ng for 4 hr using the ligation buffer described above. The ligation products were used to transform competent HW87 as has been described. Ampicillin resistant transformants were selected on L-agar plates containing 100 mcg $ml^{-1}$ ampicillin.

9) Isolation of Plasmid DNA

Plasmid DNA was prepared from the colonies containing potential horseradish peroxidase clones essentially as described (Ish-Horowicz, D., Burke, J. F. *Nucleic Acids Research* 9 2989-2998 (1981).

10) Dideoxy Sequencing

The protocol used was essentially as has been described (Biggin, M. D., Gibson, T. J., Hong, G. F. *P.N.A.S.* 80 3963-3965 (1983)). The method was modified to allow sequencing on plasmid DNA as described (Guo, L-H., Wu, R. *Nucleic Acids Research* 11 5521-5540 (1983).

11) Transformation

Transformation was accomplished using standard procedures. The strain used as a recipient in the cloning was HW87 which has the following genotype:

araD139(ara-leu)del7697 (lacIPOZY)del74 galU galK hsdR rpsL srl recA56

Any other standard cloning recipient such as HB101 would be adequate.

EXAMPLE 2

The front end of the synthetic HRP gene prepared in Example 1 was modified by the replacement of the HindIII-HpaI fragment with a synthetic linker carrying an NdeI site on the initiator ATG as follows:

```
           M  Q  L  T . . .
AAGCTTCATATGCAGTTAACC.........
HindIII     NdeI    HpaI
```

EXAMPLE 3

Expression of the Synthetic Horseradish Peroxidase Gene in *Escherichia coli*

The synthetic HRP gene of Example 2 was cloned into the expression vector pGC517 on a NdeI-BamHI fragment to give the plasmid pSD18. The host vector pGC517 was prepared from the known plasmid pAT153 (Twigg & Sherratt *Nature* 283, 216-218 (1980)), which is now a standard *E. coli* high expression vector, by the incorporation by standard methods of the known tac promoter sequence and a termination sequence. pAT153 is itself a derivative of pBR322. In pGC517 the HRP gene is expressed from the powerful and regulatable tac promoter. To ensure that expression remained repressed in uninduced cultures the plasmid was maintained in *E. coli* strain W3110 $lacI^q$, which is widely available, in which the lac repressor protein is over-produced. FIG. 5 depicts the structure of pSD18.

Strain W3110 $lacI^q$-pSD18 was grown in M9 minimal medium containing 0.2% glucose and 0.2% casamino acids. At an O.D. of 0.2-0.3 the culture was induced by the addition of IPTG to a final concentration of 5 mM. The culture was grown for a further 3 hr with samples removed at 30 min intervals.

Microscopic examination of the induced culture revealed the presence of inclusion bodies, characteristic of the accumulation of large amounts of insoluble aggregated protein within the cell. In addition, cultures expressing HRP at high levels acquired a pink colouration, perhaps related to the overexpression of a haem protein. SDS/PAGE analysis subsequently revealed the presence of a large amount of a 33 kD protein, estimated at 10-20% of total cell protein in induced but not uninduced cultures. Western blot analysis confirmed that this protein was HRP.

Standard methods for inclusion body isolation could be applied to obtain a substantial purification of the denatured HRP as insoluble aggregates. This material was then dissolved in 6M guanidine HCl prior to renaturation. For renaturation, the dissolved HRP was dialysed against 8M urea, 50 mM Tris HCl, 100 mM NaCl for 24 hr. $Ca^{2+}$ was then added (as $CaCl_2$) to 1 mM and the sample incubated for 2 hr at room temperature. This procedure resulted in the recovery of about 0.125% of the expected HRP activity by the standard pyrogallol colorimetric assay and based on the protein concentration and estimated purity of the preparation (see Table 1).

TABLE 1

Renaturation of HRP Expressed in *E. coli*

| Sample | Conditions | Rate of reaction (maximum) AU/min | Amount of recombinant HRP C assayed mcg | Activity AU/min mcg rec. HRP | Activity (% of max. activity of commercial HRP) |
|---|---|---|---|---|---|
| 1 | before 1st dialysis | 0.01 AU/ 0.8 min | 25 mcg | $5 \times 10^{-3}$ AU/min mcg | 0.007% |
| 2 | after 1st dialysis | 0.15 AU/ 1.1 min | 5.77 mcg | 0.0024 AU/min mcg | 0.034% |
| 3 | sample 2 incubated with 1 mM $Ca^{2+}$ for 2h | 0.01 AU/ 1.5 min | 0.76 mcg | 0.029 AU/min mcg | 0.125% |

Control samples prepared from similar cultures carrying the expression plasmid without the HRP gene gave backgrounds about 1000 fold less than this. The assay mixture contained freshly prepared pyrogallol and peroxide in the following concentrations: 11 mM K phosphte, pH 6.0, 8 mM $H_2O_2$, 0.55% w/v pyrogallol in $H_2O$. The HRP was added and the increase in adsorption at 420 nm was followed.

Thus the synthetic HRP gene is capable of high level expression in *E. coli* and is capable of directing the synthesis of active product.

EXAMPLE 4

The synthetic HRP gene of Example 2 was modified as follows to allow for its efficient expression in mammalian cells:

(a) The 3' end of the gene was extended from the Pst 1 site to include the C-terminal extension reported by Fujiyama et al. *Eur. J. Biochem.* 173, 681-687 (1988).

(b) The 5' end of the gene was modified by the addition of a HindIII/HpaI linker which encoded a signal sequence based on an immunoglobulin signalpeptide.

The modified HRP gene is depicted in FIG. 6, and will be referred to as HPRX.

EXAMPLE 5

Expression of the Synthetic Horesradish Peroxidase Gene in Mammalian Cells

The HRPX gene of Example 4 was inserted into the mammlian cell expression vector pCPH11 to give pCP21, in which the HRP gene is expressed from the HCMV (Human Cytomegalovirus) early promoter, see FIG. 7. The plasmid pCPH11 is based on pUC18, which is widely available and from which it can be prepared by standard methods, using the information in FIG. 7.

The HRP expression plasmid pCP21 was transfected into COS cells using the standard technique of calcium phosphate precipitation (20 mcg DNA transfected per $10^6$ cells). HRP activity was assayed in cell culture medium, 48-72 h post transfection using tetra-methyl benzidine substrate (TMB), a standard HRP reagent. No HRP activity was detectable in control constructs which did not contain a signal sequence and/or the 3' extension. In contrast, HRP activity was clearly detectable in cells transfected with pCP21 (up to 10x greater than in controls). The results are shown in Table 2.

TABLE 2

HRP Expression in COS Cells

| Vol. Extract. (mcl) | O.D. 450 Plasmid pCP21 | pCP22 | pCP11 | pCP12 |
|---|---|---|---|---|
| 100 | .004 | .022 | .008 | .003 |
| 50 | .033 | .012 | .010 | .013 |
| 25 | .107* | .010 | .003 | .016 |
| 10 | .084* | .011 | .007 | .017 |
| 5 | .064* | .015 | .012 | .011 |
| 1 | .028 | .008 | .007 | .007 |

KEY
pCP21 HRP with N and C terminal signals, correct orientation.
pCP22 HRP with N and C terminal signals, wrong orientation.
pCP11 HRP with no signal sequences, correct orientation.
pCP12 HRP with no signal sequences, wrong orientation.
All results are the mean of duplicate samples.
*significant level of activity.

HRP Assay

For assaying cell extracts, a substrate mix was prepared as follows:

TMB (3,3',5,5' tetramethyl benzidine (Sigma)) was dissolved to 10 mg/ml in DMSO and 100 mcl of this solution added to 100 ml of assay buffer (0.1M NaAc in citric acid, pH6.0) along with 100 mcl $H_2O_2$.

A cell extract was prepared by collecting the cells by centrifugation followed by freeze thawing or sonication. The medium, cell lysates and standards were aliquoted in 96 well microtitre plates as follows:

| Sample | 100 | 50 | 25 | 10 | 5 | 1 | mcl |
|---|---|---|---|---|---|---|---|
| Assay Buffer | 0 | 50 | 75 | 90 | 95 | 99 | mcl |

Blank samples were set up using 100 mcl of assay buffer alone. 100 mcl of TMB/$H_2O_2$ mix was added to the samples of incubated at RT for 30 mins to 1 hour. The reaction was stopped by the addition of 50 mcl of 2.5M $H_2SO_4$ and the colour change read at 450 nm on a plate reader.

Commercially available HRP was used as a standard diluted by a factor of $10^{-6}$.

I claim:

1. The DNA sequence of FIG. 6, which encodes horseradish peroxidase C.

2. A DNA construct comprising the sequence of FIG. 6 fused to a second DNA sequence, said DNA construct encoding a hybrid protein exhibiting horseradish peroxidase C activity.

* * * * *